(12) United States Patent
Van Meir et al.

(10) Patent No.: US 7,652,033 B2
(45) Date of Patent: Jan. 26, 2010

(54) HIF-1 INHIBITORS

(75) Inventors: Erwin G Van Meir, Tucker, GA (US); Chalet Tan, Duluth, MN (US); Anthony Roecker, La Jolla, CA (US); Kyriacos C. Nicolaou, La Jolla, CA (US)

(73) Assignee: Emory University, Atlanta, GA (US)

( * ) Notice: Subject to any disclaimer, the term of this patent is extended or adjusted under 35 U.S.C. 154(b) by 641 days.

(21) Appl. No.: 10/550,286

(22) PCT Filed: Mar. 29, 2004

(86) PCT No.: PCT/US2004/009548

§ 371 (c)(1), (2), (4) Date: Feb. 9, 2006

(87) PCT Pub. No.: WO2004/087066

PCT Pub. Date: Oct. 14, 2004

(65) Prior Publication Data

US 2007/0099952 A1  May 3, 2007

Related U.S. Application Data

(60) Provisional application No. 60/458,218, filed on Mar. 27, 2003.

(51) Int. Cl.
*A61K 31/44* (2006.01)
(52) U.S. Cl. .................................................. 514/303
(58) Field of Classification Search .................. 514/303
See application file for complete search history.

(56) References Cited

OTHER PUBLICATIONS

Nicolaou et al., J. Am. Chem. Soc. 2000, vol. 122, pp. 9939-9953.*
Cancer and Metastasis Reviews (1998), 17(1), 91-106.*
Science (1999), vol. 286, 531-537.*
Natural Product-like Combinatorial Libraries Based on Privileged Structures. 3. The "Libraries from Libraries" Principle for Diversity Enhancement of Benzopyran Libraries, Nicolaou, K.C., Pfefferkorn, J.A., Barluenga, S., Mitchell, H.J., Roecker, A.J., and Cao, G. -Q., J. Am. Chem. Soc. 2000, 122, 9968-9976.

* cited by examiner

*Primary Examiner*—Rebecca L Anderson
(74) *Attorney, Agent, or Firm*—Thomas, Kayden, Horstemeyer & Risley, LLP

(57) ABSTRACT

HIF-1 inhibitors and methods of their use are provided. In particular, 2,2-dimethylbenzopyran based compounds and methods of their use, for example in the treatment or prevention of hypoxia-related pathologies are provided.

2 Claims, 9 Drawing Sheets

Ref. No. 6

Ref. No. 3

Ref. No. 8

Ref. No. 9

Ref. No. 10

Ref. No. 11

Ref. No. 16

Ref. No. 17

Ref. No. 18

Ref. No. 19

Ref. No. 20

Ref. No. 21

Ref. No. 22

Ref. No. 23

Ref. No. 24

Ref. No. 25

Ref. No. 26

HIF-1 INHIBITORS

CROSS REFERENCE TO RELATED APPLICATION

This application is a 371 of PCT/US04/09548 filed Mar. 29, 2004.

This application claims priority to and benefit of U.S. Provisional Patent Application No. 60/458,218 filed on Mar. 27, 2003, which is incorporated by reference in its entirety.

STATEMENT REGARDING FEDERALLY SPONSORED RESEARCH OR DEVELOPMENT

This invention was made with government support under Contract No.: CA46446 from the National Institute of Health. The U.S. government has certain rights in the invention.

BACKGROUND 1. Technical Field

The present disclosure is generally directed to inhibitors of Hypoxia Inducible Factor (HIF-1), more particularly to 2,2-dimethylbenzopyran compounds, derivatives thereof, and methods of their use including but not limited to anti-tumor therapies and disorders leading to ischemia (stroke, ischemic heart disease, etc.). 2. Related Art According to the American Cancer Society, approximately 1.3 million Americans are estimated to be diagnosed with invasive cancer in 2003. The National Cancer Institutes estimates that approximately 8.9 million Americans had a history of cancer in 2003, and approximate 1,500 cancer-related deaths per day are expected in 2003. Because of the staggering number of cancer-related deaths and new cases, new medicines and methods of treatment are needed. Although recent advances have increased our understanding of some of the mechanisms leading to cancer, effective treatments for cancer remain in high demand.

Cancer can be a fatal disease, in part, because cancer can spread or metastasize throughout an organism. Metastasis plays a major role in the morbidity and mortality of breast cancer (Ford, K. et al. Breast cancer screening, diagnosis, and treatment. Dis. Mon., 45: 333-405 (1999)). Breast cancer metastasizes in a stereotypical pattern resulting in lesions found in the lymph node, lung, liver, and bone marrow. Generally, cancer cells lose differentiated properties, proper tissue compartmetalization, cell-cell attachment as well as obtain altered cell substratum attachment, altered cytoskeletal organization, cell locomotion, and the ability to survive at distant sites.

Treatments for invasive cancers such as breast cancer historically include surgery, radiation, anti-hormonal therapy, and chemotherapy. Although each therapy has some degree of success, the failure to achieve a cure in approximately 70% of patients is due to a primary lack of therapeutic effect on undetected or detected metastases and to acquired drug and hormonal resistance during therapy (Fidler, I. and Nicolson, G. L. Concepts and mechanisms of breast cancer metastases. In Bland, K. I., Copeland, E. M. (eds): The Breast. Philadelphia: WB Saunders, 1991, p 395).

Hypoxia is a major hindrance to effective solid tumor therapy. The microenvironment of rapid growing solid tumors is associated with increased energy demand and diminished vascular supply, resulting in focal areas of prominent hypoxia, regions with reduced oxygen tensions (Folkman J. What is the evidence that tumors are angiogenesis dependent? J Natl Cancer Inst 82, 4-6(1989)). Tissue oxygen electrode measurements taken in cancer patients showed a median range of oxygen partial pressure of 10 to 30 mmHg, with a significant proportion of readings below 2.5 mmHg, whereas those in normal tissues ranged from 24 to 66 mg (Vaupel P. W. Oxygenation of solid tumors. In Drug Resistance in Oncology. Teicher, B. A. (ed.) 53-85 (Marcel Dekker, New York, 1993). In the absence of oxygen, which is the most electron-affinic molecule in cells and reacts chemically with the fundamental biological lesion produced by ionizing radiation, radiotherapy is severely compromised in its ability to kill hypoxic tumor cells (Gray L. H. et al. Concentration of oxygen dissolved in tissues at the time of irradiation as a factor in radiotherapy. Br J Radiol 26, 638-648 (1953). On the other hand, hypoxia (and possibly hypoxia-associated deficiencies in other nutrients such as glucose) causes tumor cells to stop or slow their rate of progression through the cell cycle (Amellem O, Pettersen E O. Cell inactivation and cell cycle inhibition as induced by extreme hypoxia: the possible role of cell cycle arrest as a protection against hypoxia-induced lethal damage. Cell Prolif 24, 127-141 (1991)). Because most anticancer drugs are more effective against rapidly proliferating cells than slowly or non-proliferating cells, this slowing of cell proliferation leads to decreased cell killing. Chemotherapy is further affected by hypoxia as chemotherapeutic drugs are delivered systemically and the diffusion of these into the tumor makes the hypoxic regions exposed to less drug than the oxygenated cells proximal to the vessels. Moreover, the multidrug resistance (MDR1) gene product P-glycoprotein is induced by ambient hypoxia (Comerford K. M. et al. Hypoxia-inducible factor-1-dependent regulation of the multidrug resistance (MDR1) gene. Cancer Res 62, 3387-94 (2002)). Hypoxia also drives genetic changes in tumors such as loss of p53 tumor suppressor gene (Brown, J. M., and Giaccia, A. J. The unique physiology of solid tumors: opportunities (and problems) for cancer therapy. Cancer Res. 58(7): 1408-16 (1998)).

Finally, hypoxic regions are expected to be less amenable to immunotherapy due to distance from nearby vessels and compromised lymphocyte function in a hypoxic environment. Tumor cells in this aberrant environment are therefore often resistant to radio- and chemotherapy (reviewed in Brown, J. M., and Giaccia, A. J. The unique physiology of solid tumors: opportunities (and problems) for cancer therapy. Cancer Res. 58(7):1408-16 (1998).

Accordingly, there is a need for new and effective treatments for cancer. In particular, there is a need for new and effective treatments that address hypoxia and its role in hyperproliferative pathologies.

SUMMARY

Generally, aspects of the present disclosure are directed to 2,2-dimethylbenzopyran compounds and derivatives thereof, and the use of these compounds and derivatives as HIF-1 inhibitors, for example in the treatment of ischemic diseases, proliferative diseases such as cancer, and hypoxia-related pathologies. One aspect provides a composition comprising a compound of formula (I):

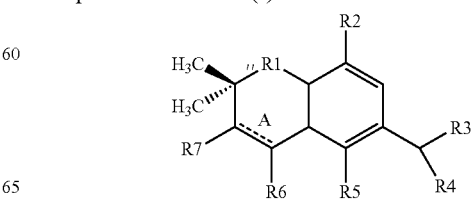

wherein

A is a π bond or absent;

R1 is O, S, or F;

R2 is H, OH, branched or unbranched $C_{1-12}$ alkyl, alkoxy, aryl, heterocycle, imidazole, alkyl substituted aryl, halo substituted aryl, halo, amine, or acyl;

R3 is H, OH, branched or unbranched $C_{1-12}$ alkyl, alkoxy, aryl, heterocycle, imidazole, substituted imidazole, alkyl substituted aryl, halo substituted aryl, halo, amine, acyl, or Z, wherein Z is $NH_2$,

—N(CH$_2$)$_2$NH$_2$, —N(CH$_2$NH$_2$)C(O)CH$_3$, —NC(O)CH$_2$NH$_2$,

—N(C(O)NH$_2$)CH$_2$CH$_3$, or wherein R8 is H, OH, alkyl, alkoxy, or halo;

R4, R6 and R7 are independently H, OH, branched or unbranched $C_{1-12}$ alkyl, alkenyl, alkoxy, aryl, heterocycle, imidazole, substituted imidazole, alkyl substituted aryl, halo substituted aryl, halo, amine, or acyl;

R5 is H, OH, halo, alkyl, or alkoxy; or a pharmaceutically acceptable salt or prodrug thereof.

Another aspect provides a composition comprising a compound of formula (II):

wherein

A is a π bond or absent;

R2 is H, OH, branched or unbranched $C_{1-12}$ alkyl, alkoxy, aryl, heterocycle, imidazole, alkyl substituted aryl, halo substituted aryl, halo, amine, or acyl;

R3 is H, OH, branched or unbranched $C_{1-12}$ alkyl, alkoxy, aryl, heterocycle, imidazole, substituted imidazole, alkyl or alkoxy substituted aryl, halo substituted aryl, halo, amine, acyl, or Z, wherein Z is $NH_2$,

—N(CH$_2$)$_2$NH$_2$, —NC(O)CH$_2$NH$_2$, —N(C(O)NH$_2$)CH$_2$CH$_3$,

—N(CH$_2$NH$_2$)C(O)CH$_3$, or wherein R8 is H, OH, alkyl, alkoxy, or halo;

R4, R6, and R7 are independently H, OH, branched or unbranched $C_{1-12}$ alkyl, alkenyl, alkoxy, aryl, heterocycle, imidazole, substituted imidazole, alkyl substituted aryl, halo substituted aryl, halo, amine, acyl;

R5 is H, OH, halo, alkyl, or alkoxy;

R9 is H, OH, halo, alkoxy, alkyl, or aryl; or a pharmaceutically acceptable salt or prodrug thereof.

Still another aspect provides a composition comprising a compound of formula (III):

wherein

A is a π bond or absent;

R3 is H, OH, branched or unbranched $C_{1-12}$ alkyl, alkoxy, aryl, heterocycle, imidazole, substituted imidazole, alkyl substituted aryl, halo substituted aryl, halo, amine, acyl, or Z, wherein Z is $NH_2$,

—N(CH$_2$)$_2$NH$_2$, —NC(O)CH$_2$NH$_2$, —N(CH$_2$NH$_2$)C(O)CH$_3$,

—N(C(O)NH$_2$)CH$_2$CH$_3$, or wherein R8 is H, OH, alkyl, alkoxy, or halo;

R4 is H, OH, branched or unbranched $C_{1-12}$ alkyl, alkenyl, alkoxy, aryl, heterocycle, imidazole, substituted imidazole, alkyl substituted aryl, halo substituted aryl, halo, amine, acyl; or a pharmaceutically acceptable salt or prodrug thereof.

Other aspects provides pharmaceutical compositions including one or more of compounds of Formula I-III, pharmaceutically acceptable salts, prodrugs, or derivatives thereof.

Other aspects provide methods of inhibiting HIF-1 including, but not limited to, a method for treating a hypoxia-related pathology in host in need of such treatment by administering an HIF-1 inhibiting amount of a compound of formula I-III, pharmaceutically acceptable salt, prodrug, derivative, or a combination thereof.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

DETAILED DESCRIPTION

Figure 1A:
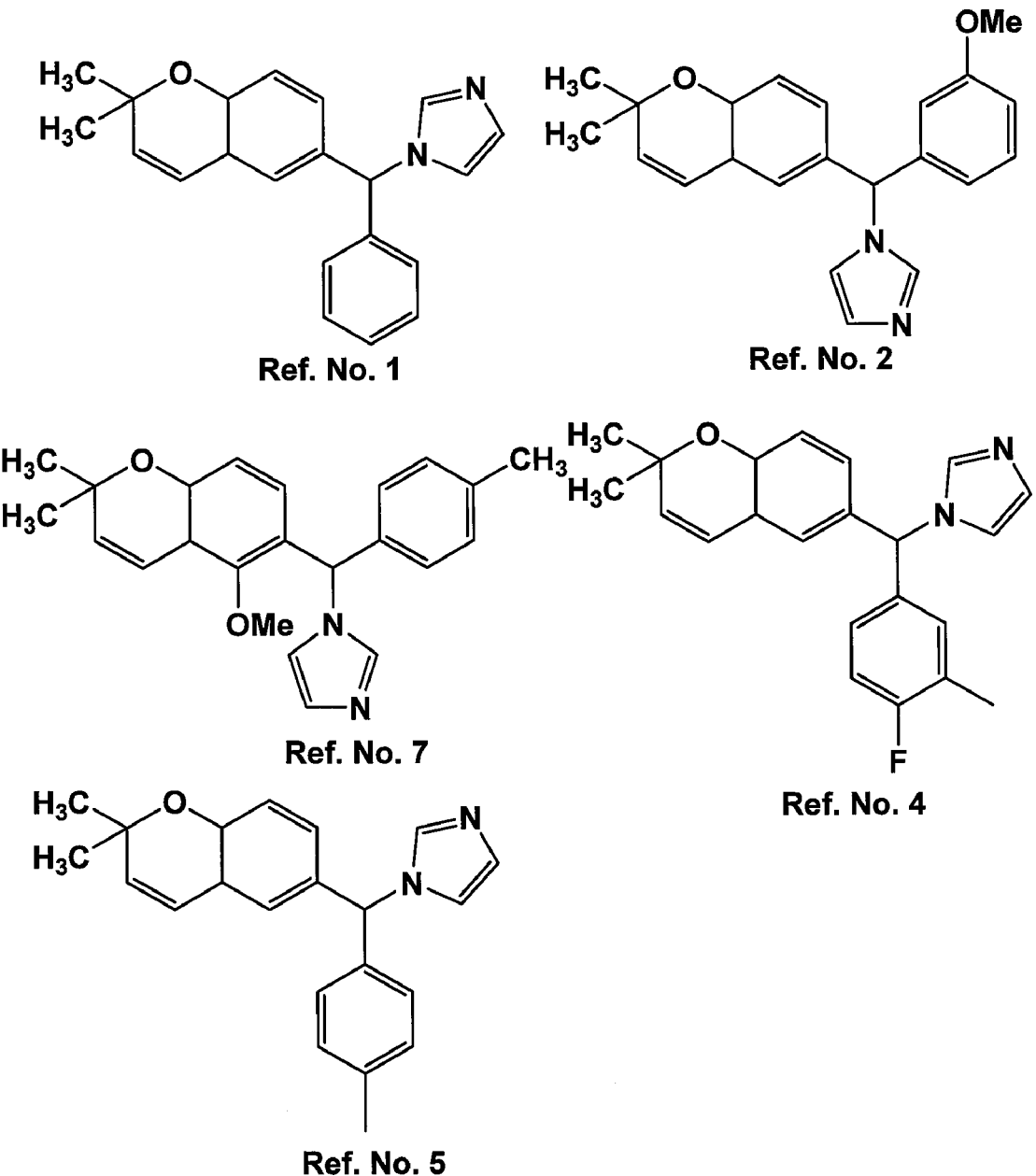
FIGS. 1A-F are chemical structures of exemplary compounds of the present disclosure.
Figure 1B:
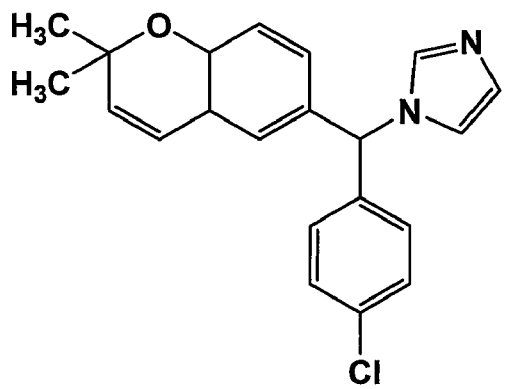
Figure 1B:
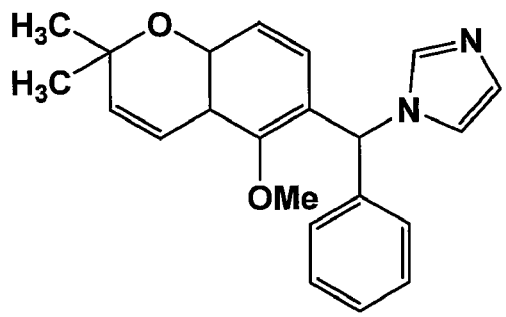
Figure 1B:
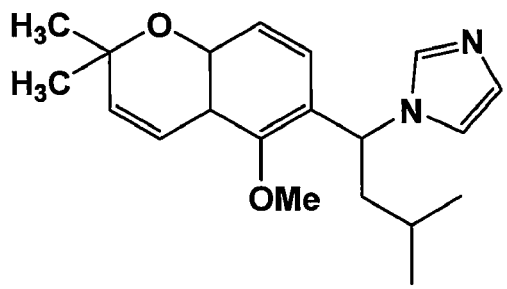
Figure 1B:
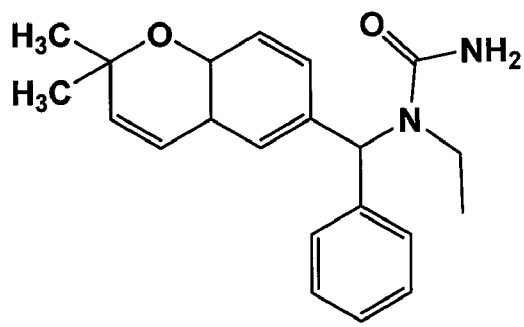
Figure 1B:
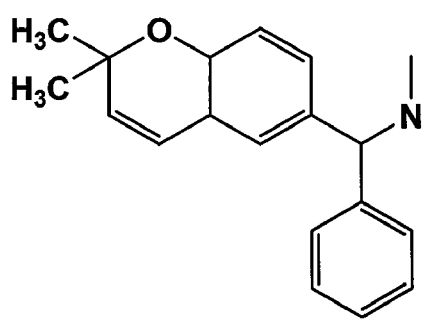
Figure 1B:
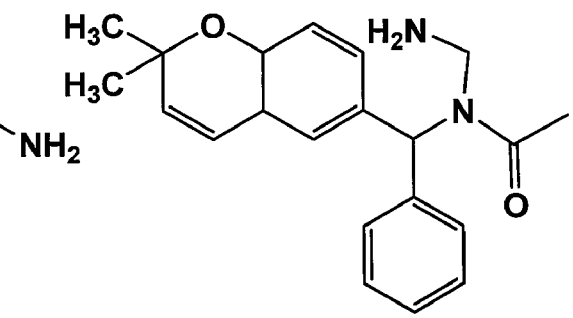
Figure 1C:
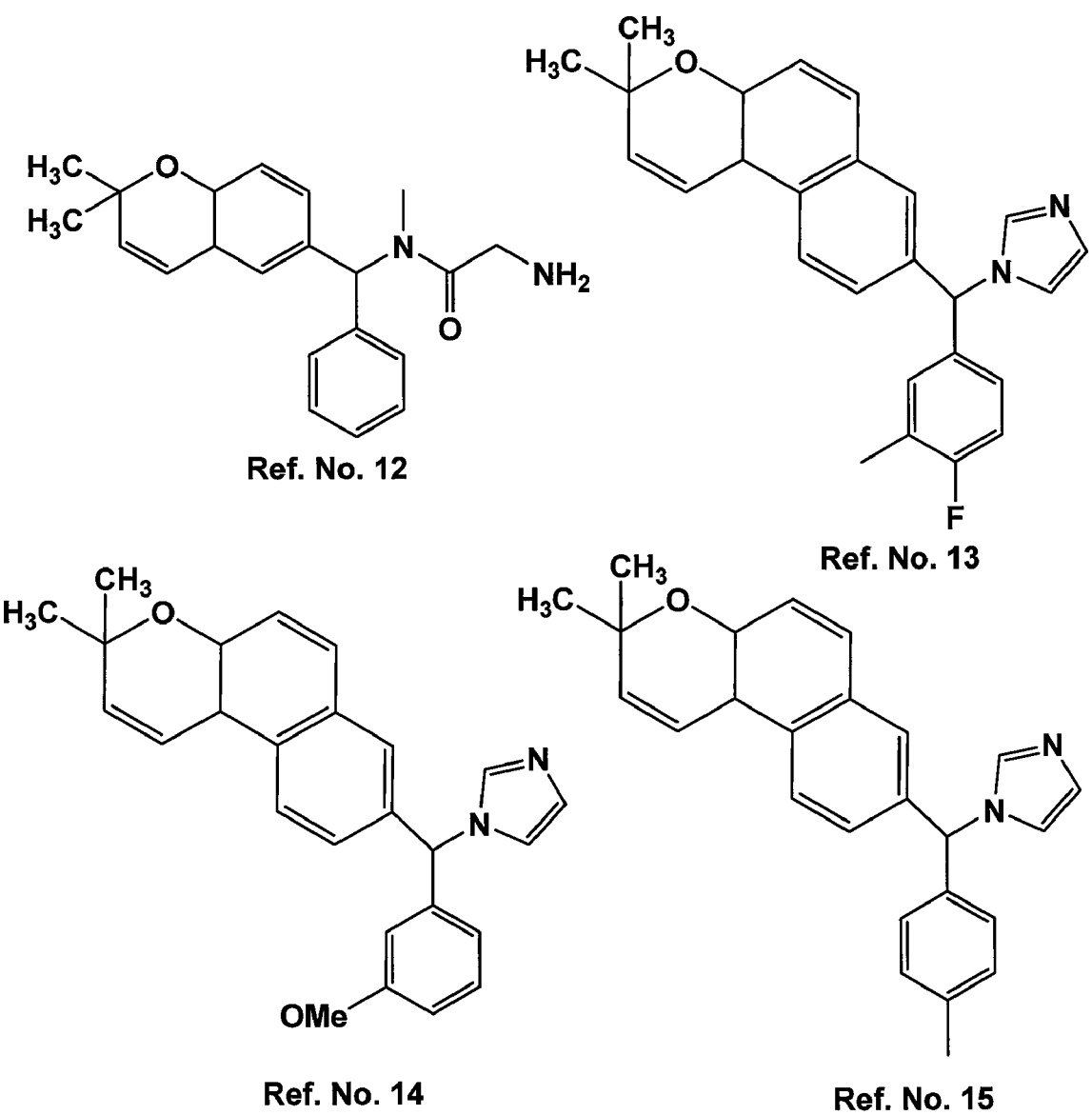
Figure 1D:
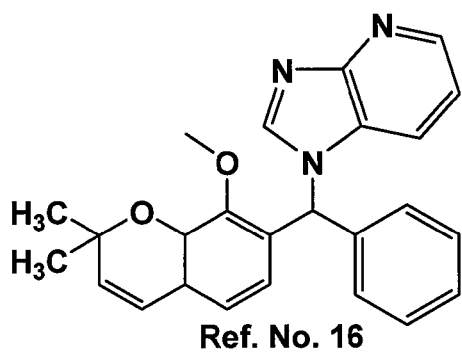
Figure 1D:
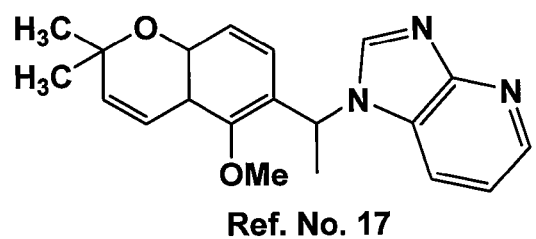
Figure 1D:
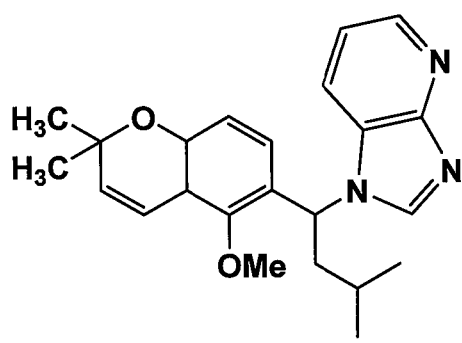
Figure 1D:
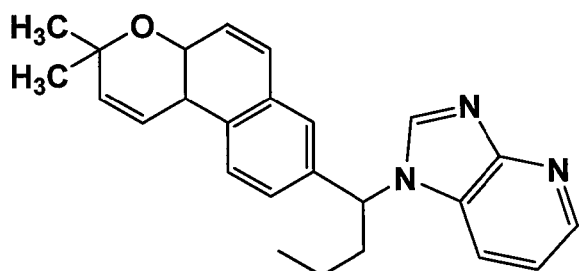
Figure 1D:
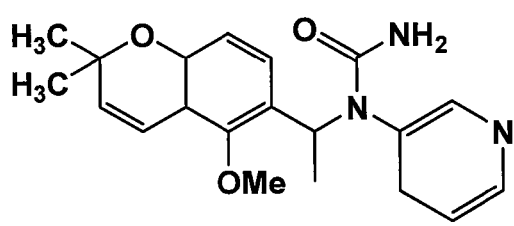
Figure 1E:
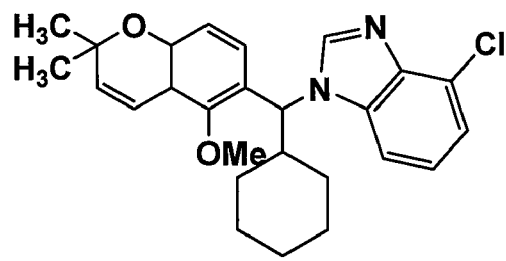
Figure 1E:
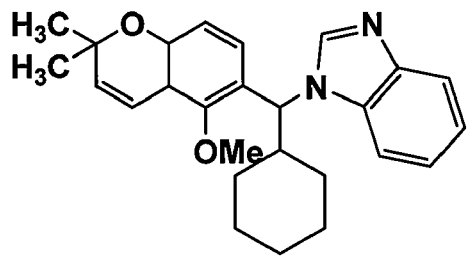
Figure 1E:
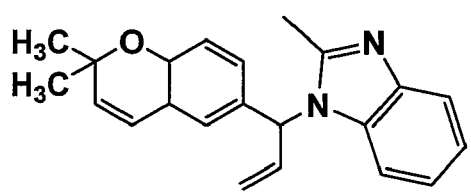
Figure 1E:
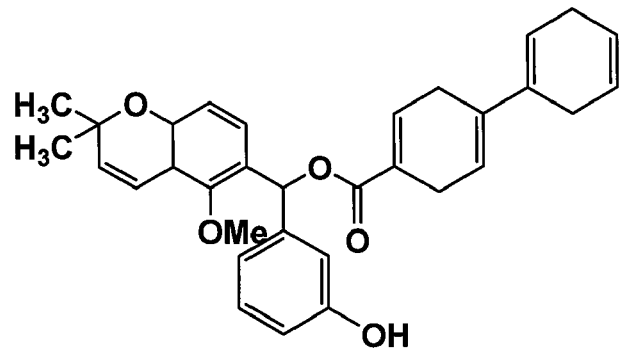
Figure 1E:
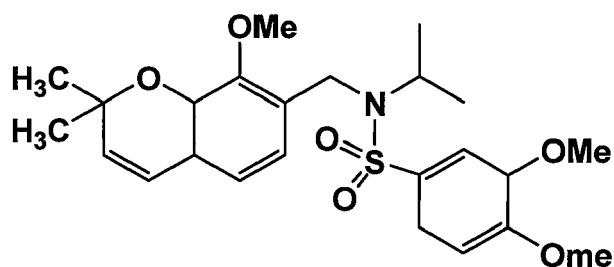
Figure 1E:
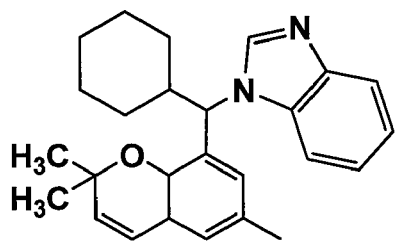
Figure 1F:
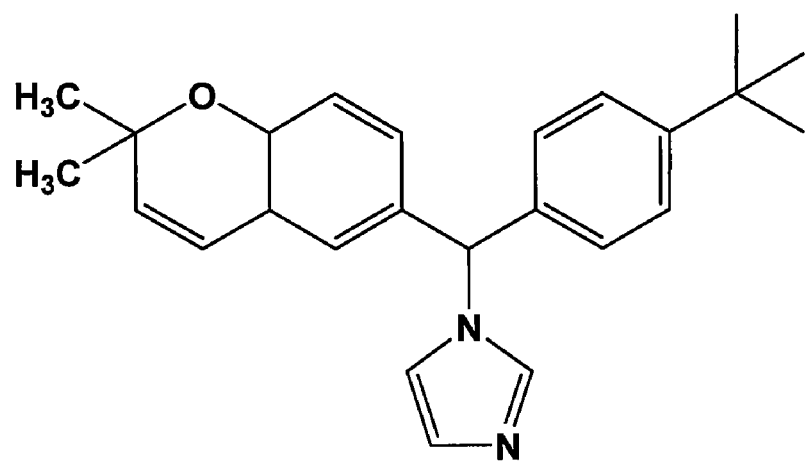

The present disclosure may be understood more readily by reference to the following detailed description and the Examples included therein.

Before the present compounds, compositions and methods are disclosed and described, it is to be understood that this disclosure is not limited to specific pharmaceutical carriers, or to particular pharmaceutical formulations or administration regimens, as such may, of course, vary. It is also to be understood that the terminology used herein is for the purpose of describing particular embodiments only and is not intended to be limiting.

1. Definitions

The term "organism" or "host" refers to any living entity comprised of at least one cell. A living organism can be as simple as, for example, a single eukaryotic cell or as complex as a mammal, including a human being.

The term "HIF-1 inhibitor" means a compound, pharmaceutically acceptable salt, prodrug, or derivative thereof that inhibits the biological activity of HIF-1, interferes with the HIF-1 signal transduction pathway, or down regulates expression or availability of HIF-1 in a cell or organism.

The term "hypoxia-related pathology" means a pathology that is caused in part, either directly or indirectly, by conditions of below typical physiological amounts of oxygen. The term includes cancer, cancer metastasis, ischemia, stroke and related conditions, diseases, or syndromes.

The term "derivative" means a modification to the disclosed compounds including but not limited to hydrolysis, reduction, or oxidation products of the disclosed compounds. In particular, the term encompasses opening of a nitrogen containing ring structure, including but not limited to an imidazole, of the disclosed compounds. Hydrolysis, reduction, and oxidation reactions are known in the art.

The term "therapeutically effective amount" as used herein refers to that amount of the compound being administered which will relieve to some extent one or more of the symptoms of the disorder being treated. In reference to cancer or pathologies related to unregulated cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer, (5) prevention the formation of cancer by application of the compound (like sun screen to protect against cancer), and/or (6) to prevent the chain of events downstream of an initial ischemic condition which leads to the pathology.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer, these terms simply mean that the life expectancy of an individual affected with a cancer will be increased or that one or more of the symptoms of the disease will be reduced.

The term "prodrug" refers to an agent which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. *Progress in Drug Research,* 4:221-294; Morozowich et al. (1977). Application of Physical Organic Principles to Prodrug Design in E. B. Roche ed. *Design of Biopharmaceutical Properties through Prodrugs and Analogs*, APhA; Acad. Pharm. Sci.; E. B. Roche, ed. (1977). *Bioreversible Carriers in Drug in Drug Design, Theory and Application*, APhA; H. Bundgaard, ed. (1985) *Design of Prodrugs*, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., *Transport Processes in Pharmaceutical Systems*, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.*, 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.*, 72(3): 324-325; Han, H. K. et al. (2000). Targeted prodrug design to optimize drug delivery, *AAPS PharmSci.*, 2(1): E6; Sadzuka Y. (2000). Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl 2:S15-27; Wang, W. et al. (1999) Prodrug approaches to the improved delivery of peptide drugs. *Curr. Pharm. Des.*, 5(4):265-87.

As used herein, the term "topically active agents" refers to compositions of the present disclosure that elicit pharmacological responses at the site of application (contact) to a host.

As used herein, the term "topically" refers to application of the compositions of the present disclosure to the surface of the skin and mucosal cells and tissues.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred. The term "substituted alkyl" refers to alkyl groups substituted with one or more groups, preferably selected from aryl, substituted aryl, heterocycle, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The term "alkoxy" means an alkyl group linked to oxygen thus: R—O—. In this function, R represents the alkyl group. An example would be the methoxy group $CH_3O$—.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The terms "cycloalkyl" and "cycloalkenyl" refer to mono-, bi- or tri homocylcic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g. fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

The disclosed compounds form salts which are also within the scope of this invention. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein, Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The disclosed compounds which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The disclosed compounds which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the disclosure are also contemplated herein. Solvates of the compounds are preferably hydrates.

To the extent that the disclosed compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The terms "including", "such as", "for example" and the like are intended to refer to exemplary embodiments and not to limit the scope of the present disclosure.

2. Hypoxia Inducible Factor (HIF-1)

HIF-1 is a primary transcriptional factor responsible for specific induction of genes in hypoxia. HIF-1 is composed of two subunits belonging to the bHLH-PAS family: HIF-1α and aryl hydrocarbon receptor nuclear translocator (ARNT also known as HIF-1β). To activate transaction of target genes, HIF-1α dimerizes with HIF-1β and binds to consensus sequences (hypoxia responsive element, HRE) in the promoter or enhancer regions of these genes. Proteins encoded by such genes include vascular endothelial growth factor (VEGF), erythropoietin, glucose transporter-1, glycolytic enzymes and tyrosine hydroxylase (Semenza G. L. Regulation of mammalian of homeostasis by hypoxia-inducible factor 1. Annu Rev Cell Dev Biol 15, 551-78 (1999)).

In normoxia, von Hippel Lindau protein (pVHL) organizes the assembly of a complex that activates the E3 ubiquitin ligase which then ubiquitinylates HIF-1α, targeting its degradation. The interaction between HIF-1α and pVHL is regulated through hydroxylation of two proline residues of HIF-1α by a prolyl hydroxylase. In the absence of oxygen, this enzyme is no longer active and HIF-1α does not interact with pVHL and accumulates intracellularly (Ivan, M. et al. HIFα targeted for VHL-mediated destruction by proline hydroxylation: implications for $O_2$ sensing. Science 292, 464-8 (2001); Jaakkola, P. et al. Targeting of HIFα to the von Hippel Lindau ubiquitylation complex by $O_2$ regulated prolyl hydroxylation. Science 292, 468-72 (2001)).

Tumor hypoxia increases malignant progression and metastasis by promoting angiogenesis through the induction of proangiogenic proteins such as VEGF (Schweiki, D. et al. Vascular endothelial growth factor induced by hypoxia may mediate hypoxia-induced angiogenesis. Nature 359, 843-5 (1992)). Most genes induced by hypoxia are regulated by HIF-1α, this protein therefore plays a pivotal role in tumor development (Dachs G. U. and Chaplin, D. J. Microenvironmental control of gene expression: implications for tumor angiogenesis, progression, and metastasis. Semin Radiat Oncol 8, 208-16 (1998); Maxwell, P. H. et al. Hypoxia-inducible factor-1 mediates gene expression in solid tumors and influences both angiogenesis and tumor growth. Proc Natl Acad Sci USA 94, 8104-9 (1997); Semenza, G. L. Hypoxia-inducible factor 1: master regulator of $O_2$ homeostasis. Curr Opin Genet Dev 8, 588-94 (1998)). Histological analyses have shown that an increased level of intracellular HIF-1α was associated with poor prognosis and resistance to therapy in head and neck, breast, cervical and oropharyngeal cancers (Beasley, N. J. P. et al. Hypoxia-inducible factors HIF-1α and HIF-2α in head and neck cancer: relationship to tumor biology and treatment outcome in surgically resected patients. Cancer Res 62, 2493-7 (2002); Schindl, M. et al. Overexpresssion of hypoxia-inducible factor Iα is associated with an unfavorable prognosis in lymph node-positive breast cancer. Clin Cancer Res 8, 1831-7(2002); Bimer, P. et al. Overexpression of hypoxia-inducible factor Iα is a marker for an unfavorable prognosis in early-stage invasive cervical cancer. Cancer Res 60, 4693-6 (2000); Aebersold, D. M. et al. Expression of hypoxia-inducible factor-Iα: a novel predictive and prognostic parameter in the radiotherapy of oropharyngeal cancer. Cancer Res 61, 2911-6 (2001)). HIF-1α was overexpressed in the cytoplasm and the nucleus of colon, breast, gastric, lung, skin, ovarian, pancreatic, prostate and renal carcinomas.

3. HIF-1 Inhibitors

The compounds, derivatives, pharmaceutically acceptable salts, and prodrugs thereof disclosed herein have been discovered to be inhibitors of HIF-1. One embodiment provides a composition comprising a compound of formula (I):

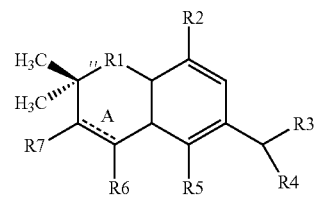

wherein

A is a π bond or absent;

R1 is O, S, or F;

R2 is H, OH, branched or unbranched $C_{1-12}$ alkyl, alkoxy, aryl, heterocycle, imidazole, alkyl substituted aryl, halo substituted aryl, halo, amine, or acyl;

R3 is H, OH, branched or unbranched $C_{1-12}$ alkyl, alkoxy, aryl, heterocycle, imidazole, substituted imidazole, alkyl substituted aryl, halo substituted aryl, halo, amine, acyl, or Z, wherein Z is $NH_2$,

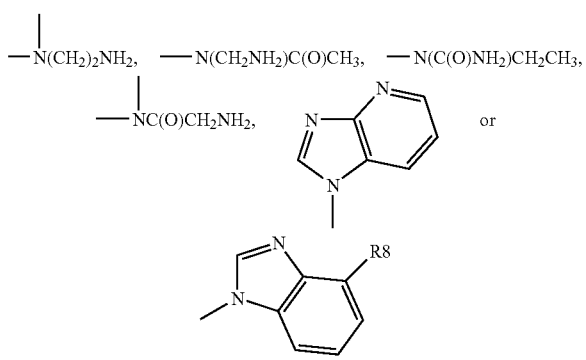

wherein R8 is H, OH, alkyl, alkoxy, or halo;

R4, R6 and R7 are independently H, OH, branched or unbranched $C_{1-12}$ alkyl, alkenyl, alkoxy, aryl, heterocycle, imidazole, substituted imidazole, alkyl substituted aryl, halo substituted aryl, halo, amine, or acyl;

R5 is H, OH, halo, alkyl, or alkoxy; or a pharmaceutically acceptable salt or prodrug thereof.

Another embodiment provides a composition comprising a compound of formula (II):

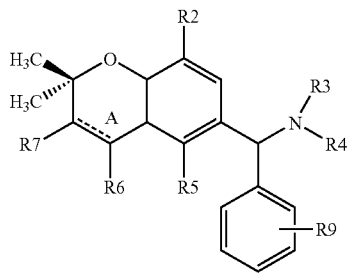

wherein

A is a π bond or absent;

R2 is H, OH, branched or unbranched $C_{1-12}$ alkyl, alkoxy, aryl, heterocycle, imidazole, alkyl substituted aryl, halo substituted aryl, halo, amine, or acyl;

R3 is H, OH, branched or unbranched $C_{1-12}$ alkyl, alkoxy, aryl, heterocycle, imidazole, substituted imidazole, alkyl or alkoxy substituted aryl, halo substituted aryl, halo, amine, acyl, or Z, wherein Z is $NH_2$,

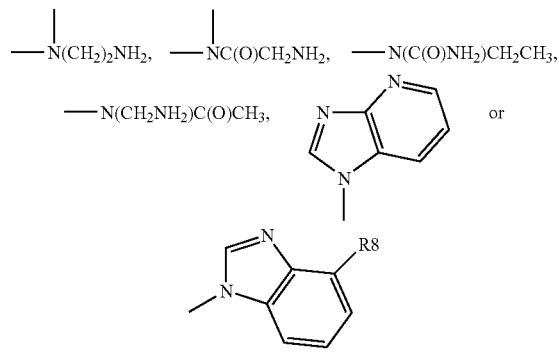

wherein R8 is H, OH, alkyl, alkoxy, or halo;

R4, R6, and R7 are independently H, OH, branched or unbranched $C_{1-12}$ alkyl, alkenyl, alkoxy, aryl, heterocycle, imidazole, substituted imidazole, alkyl substituted aryl, halo substituted aryl, halo, amine, acyl;

R5 is H, OH, halo, alkyl, or alkoxy;

R9 is H, OH, halo, alkoxy, alkyl, or aryl; or a pharmaceutically acceptable salt or prodrug thereof.

Still another embodiment provides a composition comprising a compound of formula (III):

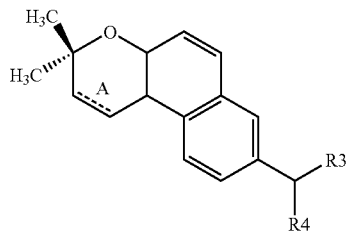

wherein

A is a π bond or absent;

R3 is H, OH, branched or unbranched $C_{1-12}$ alkyl, alkoxy, aryl, heterocycle, imidazole, substituted imidazole, alkyl substituted aryl, halo substituted aryl, halo, amine, acyl, or Z, wherein Z is $NH_2$,

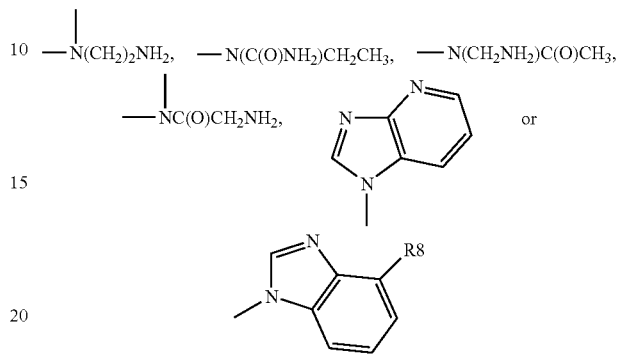

wherein R8 is H, OH, alkyl, alkoxy, or halo;

R4 is H, OH, branched or unbranched $C_{1-12}$ alkyl, alkenyl, alkoxy, aryl, heterocycle, imidazole, substituted imidazole, alkyl substituted aryl, halo substituted aryl, halo, amine, acyl; or a pharmaceutically acceptable salt or prodrug thereof.

In one embodiment the compound is selected from the group consisting of
1-[(2,2-dimethyl-2H-chromen-6-yl)(phenyl)methyl]-1H-imidazole;
1-[(2,2-dimethyl-4a,8a-dihydro-2H-chromen-6-yl)(4-methylphenyl)methyl]-1H-imidazole;
1-[(2,2-dimethyl-2H-chromen-6-yl)(3-methoxyphenyl)methyl]-1H-imidazole;
1-[(5-methoxy-2,2-dimethyl-2H-chromen-6-yl)(4-methylphenyl)methyl]-1H-imidazole;
1-[(2,2-dimethyl-2H-chromen-6-yl)(4-fluoro-3-methylphenyl)methyl]-1H-imidazole;
1-[(4-chlorophenyl)(2,2-dimethyl-2H-chromen-6-yl)methyl]-1H-imidazole;
1-[(5-methoxy-2,2-dimethyl-2H-chromen-6-yl)(phenyl)methyl]-1H-imidazole;
1-[1-(5-methoxy-2,2-dimethyl-2H-chromen-6-yl)-3-methylbutyl]-1H-imidazole;
1-[(3,3-dimethyl-7,10-dihydro-3H-benzo[f]chromen-8-yl)(4-fluoro-3-methylphenyl)methyl]-1H-imidazole;
1-[(3,3-dimethyl-7,10-dihydro-3H-benzo[f]chromen-8-yl)(3-methoxyphenyl)methyl]-1H-imidazole;
1-[(3,3-dimethyl-7,10-dihydro-3H-benzo[f]chromen-8-yl)(4-methylphenyl )methyl]-1H-imidazole;
1-[(8-methoxy-2,2-dimethyl-2H-chromen-7-yl)(phenyl)methyl]-1H-imidazo[4,5-b]pyridine;
1-[1-(5-methoxy-2,2-dimethyl-2H-chromen-6-yl)ethyl]-1H-imidazo[4,5-b]pyridine;
1-[1-(5-methoxy-2,2-dimethyl-2H-chromen-6-yl)-3-methylbutyl]-1H-imidazo[4,5-b]pyridine;
1-[1-(3,3-dimethyl-7,10-dihydro-3H-benzo[f]chromen-8-yl)-3-methylbutyl]-1H-imidazo[4,5-b]pyridine;
4-chloro-1-[cyclohexyl(5-methoxy-2,2-dimethyl-2H-chromen-6-yl)methyl]-1H-benzimidazole;
1-[cyclohexyl(5-methoxy-2,2-dimethyl-2H-chromen-6-yl)methyl]-1H-benzimidazole;
1-[1-(2,2-dimethyl-2H-chromen-6-yl)prop-2-en-1-yl]-2-methyl-1H-benzimidazole;

1-[cyclohexyl(2,2,6-trimethyl-2H-chromen-8-yl)methyl]-1H-benzimidazole;

(2,2-dimethyl-2H-chromen-6-yl)(3-hydroxyphenyl)methyl biphenyl-4-carboxylate;

N-isopropyl-3,4-dimethoxy-N-[(8-methoxy-2,2-dimethyl-2H-chromen-7-yl)methyl]benzenesulfonamide; and 1-[(4-tert-butylphenyl)(2,2-dimethyl-4a,8a-dihydro-2H-chromen-6-yl)methyl]-1H-imidazole.

In another embodiment, the compound is a derivative of the disclosed compounds, including, but not limited to, an oxidation, reduction, or hydrolysis reaction product of the disclosed compounds, particularly those compounds in which a nitrogen containing ring, for example an imidazole ring, has been opened.

Exemplary derivatives include but are not limited to, N-[(2,2-dimethyl-4a,8a-dihydro-2H-chromen-6-yl)(phenyl)methyl]-N-ethylurea; N-[(2,2-dimethyl-4a,8a-dihydro-2H-chromen-6-yl)(phenyl)methyl]-N-methylethane-1,2-diamine; N-(aminomethyl)-N-[(2,2-dimethyl-4a,8a-dihydro-2H-chromen-6-yl)(phenyl)methyl]acetamide; and $N^1$-[(2,2-dimethyl-4a,8a-dihydro-2H-chromen-6-yl)(phenyl)methyl]-$N^1$-methylglycinamide.

The disclosed compounds were synthesized using methods and techniques for benzopyran synthesis known in the art. See for example, Nicolaou, K. C. et al. Natural Product-like Combinatorial Libraries Based on Privileged Structures 1. General Principles and Solid-Phase Synthesis of Benzopyrans. J. Am. Chem. Soc. 122:9939-9953 (2000); Nicolaou, K. C. et al. Natural Product-like Combinatorial Libraries Based on Privileged Structures. 2. Construction of a 10,000-Membered Benzopyran Library by Directed Split-and-Pool Chemistry Using NanoKans and Optical Encoding. J. Am. Chem. Soc. 122:9954-9967 (2000); Nicolaou, K. C. et al. Natural Product-like Combinatorial Libraries Based on Privileged Structures Natural Product-like Combinatorial Libraries Based on Privileged Structures 3. The "Libraries from Libraries" Principle for Diversity Enhancement of Benzopyran Libraries. J. Am. Chem. Soc. 122:9968-9976 (2000), which are incorporated by reference in their entirety.

4. Methods of Use

Some embodiments of the present disclosure are directed to interfering, inhibiting, or blocking signal transduction through the HIF-1 pathway. Such inhibition can be accomplished by binding of HIF-1 or molecules associated with HIF with the disclosed compounds or their derivatives to render HIF-1 inactive or unavailable. Alternatively, the HIF-1 pathway can be inhibited, in whole or in part, by preventing the expression of HIF-1 in a cell (through preventing HIF mRNA transcription, post-transcriptional modification of HIF mRNA, translation of HIF mRNA, posttranslational modification of HIF protein and HIF stability). HIF-1 inhibition can also be achieved by interfering with the binding of HIF-1 or HIF-1 complexes to the hypoxia responsive element.

One embodiment provides a method for the treatment or prevention of a hypoxia-related pathology by administering to a host, for example a mammal, in need of such treatment, an HIF-1 inhibiting amount of disclosed compounds, compositions, derivatives, pharmaceutically acceptable salts, prodrugs, or combinations thereof.

Another embodiment provides a method of modulating HIF-1 activity in a cell, for example a eukaryotic cell, by contacting the cell with an HIF-I inhibiting amount of the disclosed compounds, compositions, derivatives, pharmaceutically acceptable salts, prodrugs, or combinations thereof.

Still another embodiment provides a method of treating or preventing cancer or a tumor in a host by administering to the host a HIF-1 inhibiting amount of the disclosed compounds, compositions, derivatives, pharmaceutically acceptable salts, prodrugs, or combinations thereof.

Another embodiment provides a method of treating psoriasis including administering to the host an HIF- inhibiting amount of the disclosed compounds, compositions, derivatives, pharmaceutically acceptable salts, prodrugs, or combinations thereof. Inhibition of HIF-1 results in the inhibition of HIF-mediated activation of VEGF, which interferes or inhibits VEGF signal transduction involved in psoriasis. It will be appreciated that the disclosed compositions can also be used to treat other VEGF mediated pathologies by interfering or inhibiting HIF- mediated activation of VEGF.

Cancer is a general term for diseases in which abnormal cells divide without control. Cancer cells can invade nearby tissues and can spread through the bloodstream and lymphatic system to other parts of the body. It has been discovered that the administration of an HIF-1 inhibitor to a host, for example a mammal, inhibits or reduces cancer, tumor growth or formation, and the metastasis of tumor cells.

There are several main types of cancer, and the disclosed compositions can be used to treat any type of cancer. For example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors. The compositions described herein can be used to reduce, inhibit, or diminish the proliferation of tumor cells, and thereby assist in reducing the size of a tumor. In particular, the disclosed compositions are useful for the treatment of solid tumors or pathologies in areas of hypoxia. Cancers can also have genetic alterations that lead to constitutive HIF expression independently of hypoxia.

Representative cancers that may treated with the disclosed compositions and methods include, but are not limited to, bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth) and continue their rapid growth and division in this new location. This is called metastasis. Once malignant cells have metastasized, achieving cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain. The compositions provided herein can be used to treat benign or malignant tumors.

Accordingly, one embodiment provides a method of modulating gene transcription, for example the transcription of VEGF, erythropoietin, glucose transporter-1, glycolytic enzymes, or tyrosine hydroxylase, in a cell, for example a tumor or cancer cell, by contacting the cell with an HIF-1 inhibiting amount of one or more of the disclosed compounds, pharmaceutical salts, prodrugs, or derivatives thereof. Alternatively, such transcription can be inhibited in a host by administering to the host an HIF-1 inhibiting amount of the disclosed compounds and compositions.

Another embodiment provides a method of modulating gene expression in a tumor cell by contacting the tumor cell with an HIF-1 modulating amount of one or more of the disclosed compounds, compositions, pharmaceutically acceptable salts, derivatives or prodrugs thereof. The modulation of the HIF-1 pathway with the disclosed compounds and compositions can occur at transcriptional, translational and/or post-translational levels. The disclosed compounds can modulate gene transcriptions by binding to HIF-1 and preventing HIF-1 from forming complexes with other molecules including DNA and proteins. For example, the disclosed compounds and compositions can bind to HIF-1 and induce conformational changes that prevent HIF-1 from interacting with its biological targets. Alternatively, the disclosed compounds can bind HIF-1 and form aggresomes or other complexes that sequester HIF-1 or otherwise physically prevent HIF-1 from interacting with other biological molecules. Finally, the disclosed compounds and compositions can inhibit or interfere with the intracellular transport of HIF-1 including, but not limited to, the translocation of HIF-1 from the cytoplasm to the nucleus.

Another embodiment provides a method for treating an hypoxia-related pathology by administering the combination of the disclosed compounds and compositions with conventional chemotherapeutic agents and/or radiotherapy. For example, the disclosed compositions can be used to treat a pathology, for example a proliferative pathology such as cancer or other hypoxia related pathology independently or in combination with one another or with one or more additional therapeutic agents. Representative therapeutic agents include but are not limited to antibiotics, anti-inflammatories, antioxidants, analgesics, radioisotopes, chemotherapeutic agents such as nascopine, paclitaxel, nocodazole, vinca alkaloids, adriamycin, alkeran, Ara-C, BiCNU, busulfan, CCNU, carboplatinum, cisplatinum, cytoxan, daunorubicin, DTIC, 5-FU, fludarabine, hydrea, idarubicin, ifosfamide, methotrexate, mithramycin, mitomycin, mitoxantrone, nitrogen, mustard, velban, vincristine, VP-16, gemcitabine (gemzar), herceptin, irinotecan, (camptosar, CPT-11), leustatin, navelbine, rituxan, STI-571, taxotere, topotecan, (hycamtin), xeloda (capecitabine), zevelin, and combinations thereof.

It will be appreciated that the compounds of the present disclosure can be used in combination with radiation therapy or surgical procedures for the treatment of a pathology, for example cancer.

In one embodiment, the disclosed composition are administered to a host having developed resistance to conventional chemotherapeutic agents.

5. Pharmaceutical Compositions

Pharmaceutical compositions and dosage forms of the disclosure comprise a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical compositions and unit dosage forms of the disclosure typically also comprise one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure comprise a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, and more preferably in an amount of from 50 mg to 500 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

5.1. Oral Dosage Forms

Pharmaceutical compositions of the disclosure that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms of the compositions of the disclosure are prepared by combining the pharmaceutically acceptable salt of disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Due to their ease of administration, tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients which are well known in the art and are listed in the USP (XXI)/NF (XVI), which is incorporated herein by reference. In general, lactose-free compositions comprise a pharmaceutically acceptable salt of an HIF-1 inhibitor, a binder/filler, and a lubricant in pharmaceutically compatible and pharmaceutically acceptable amounts. Preferred lactose-free dosage forms comprise a pharmaceutically acceptable salt of the disclosed compounds, microcrystalline cellulose, pre-gelatinized starch, and magnesium stearate.

This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

5.2 Controlled and Delayed Release Dosage Forms

Pharmaceutically acceptable salts of the disclosed compounds can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm & Haas, Spring House, Pa. USA).

One embodiment of the disclosure encompasses a unit dosage form which comprises a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull™, Delayed Push-Pull™, Multi-Layer Push-Pull™, and Push-Stick™ Systems, all of which are well known. See, e.g. worldwide website alza.com. Additional OROS® systems that can be used for the controlled oral delivery of compounds and compositions of the disclosure include OROS®-CT and L-OROS®; see, Delivery Times, vol. 11, issue 11 (Alza Corporation).

Conventional OROS® oral dosage forms are made by compressing a drug powder (e.g., a HIF-1 inhibitor salt) into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility.

Because HIF-1 inhibitor salts and complexes of this disclosure (e.g., an HIF-1 inhibitor sodium salt) may be far more soluble in water than an HIF-1 inhibitor itself, they may be well suited for osmotic-based delivery to patients. This disclosure does, however, encompass the incorporation of an HIF-1 inhibitor, and non-salt isomers and isomeric mixtures thereof, into OROS® dosage forms.

A specific dosage form of the compositions of the disclosure comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer comprises a salt of an HIF-1 inhibitor, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the disclosure comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of a HIF-1 inhibitor, or a polymorph, solvate, hydrate, dehydrate, co-crystal, anhydrous, or amorphous form thereof. See U.S. Pat. No. 6,342,249, the entirety of which is incorporated herein by reference.

5.3. Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; Water for Injection USP; saline solution; glucose solution; aqueous vehicles such as but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of a HIF-1 inhibitor disclosed herein can also be incorporated into the parenteral dosage forms of the disclosure, including conventional and controlled-release parenteral dosage forms.

5.4. Topical, Transdermal And Mucosal Dosage Forms

Topical dosage forms of the disclosure include, but are not limited to, creams, lotions, ointments, gels, shampoos, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466;465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of an HIF-1 inhibitor of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an HIF-1 inhibitor can be used to further adjust the properties of the resulting composition.

5.6. Kits

Typically, active ingredients of the pharmaceutical compositions of the disclosure are preferably not administered to a patient at the same time or by the same route of administration. This disclosure therefore encompasses kits which, when used by the medical practitioner, can simplify the administration of appropriate amounts of active ingredients to a patient.

A typical kit comprises a unit dosage form of a pharmaceutically acceptable salt of an HIF-1 inhibitor and optionally, a unit dosage form of a second pharmacologically active compound, such as anti-proliferative agent, or anti-cancer agent. In particular, the pharmaceutically acceptable salt of an HIF-1 inhibitor is the sodium, lithium, or potassium salt, or a polymorph, solvate, hydrate, dehydrate, co-crystal, anhydrous, or amorphous form thereof. A kit may further comprise a device that can be used to administer the active ingredient. Examples of such devices include, but are not limited to, syringes, drip bags, patches, and inhalers.

Kits of the disclosure can further comprise pharmaceutically acceptable vehicles that can be used to administer one or more active ingredients (e.g, an HIF-1 inhibitor). For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Other embodiments are directed to the use of the disclosed compositions in the preparation of a medicament for the treatment hypoxia-related pathology.

EXAMPLE

Genetically engineered LN229 cells (a human glioma cell line) which stably express the alkaline phosphatase reporter gene under the control of six copies of a hypoxia-responsive element was used to identify small-molecule inhibitors of HIF-1/HRE pathway. The engineered LN229 cell line is disclosed in U.S. Provisional Patent Application No. 60/235,283, which is incorporated by reference in its entirety herein, Cells were seeded at 40,000 cells per well in 96-well plates. Compounds of interest with 2,2-dimethylbenzopyran motifs were added and the plates were incubated under hypoxia (1% $O_2$, 5% $CO_2$ and 94% $N_2$) at 37° C. for 24 h. Cells were then washed with phosphate-buffered saline and incubated with p-nitrophenyl phosphate at 37° C. for 30 min. The reaction was terminated by adding 3 N NaOH and the plates were read for absorbance at 405 nm. The anti-HIF-1/HRE activity of each compound was quantified as the decrease of percentage of alkaline phosphatase (AP) activity compared to the untreated control cells.

Figure 2:
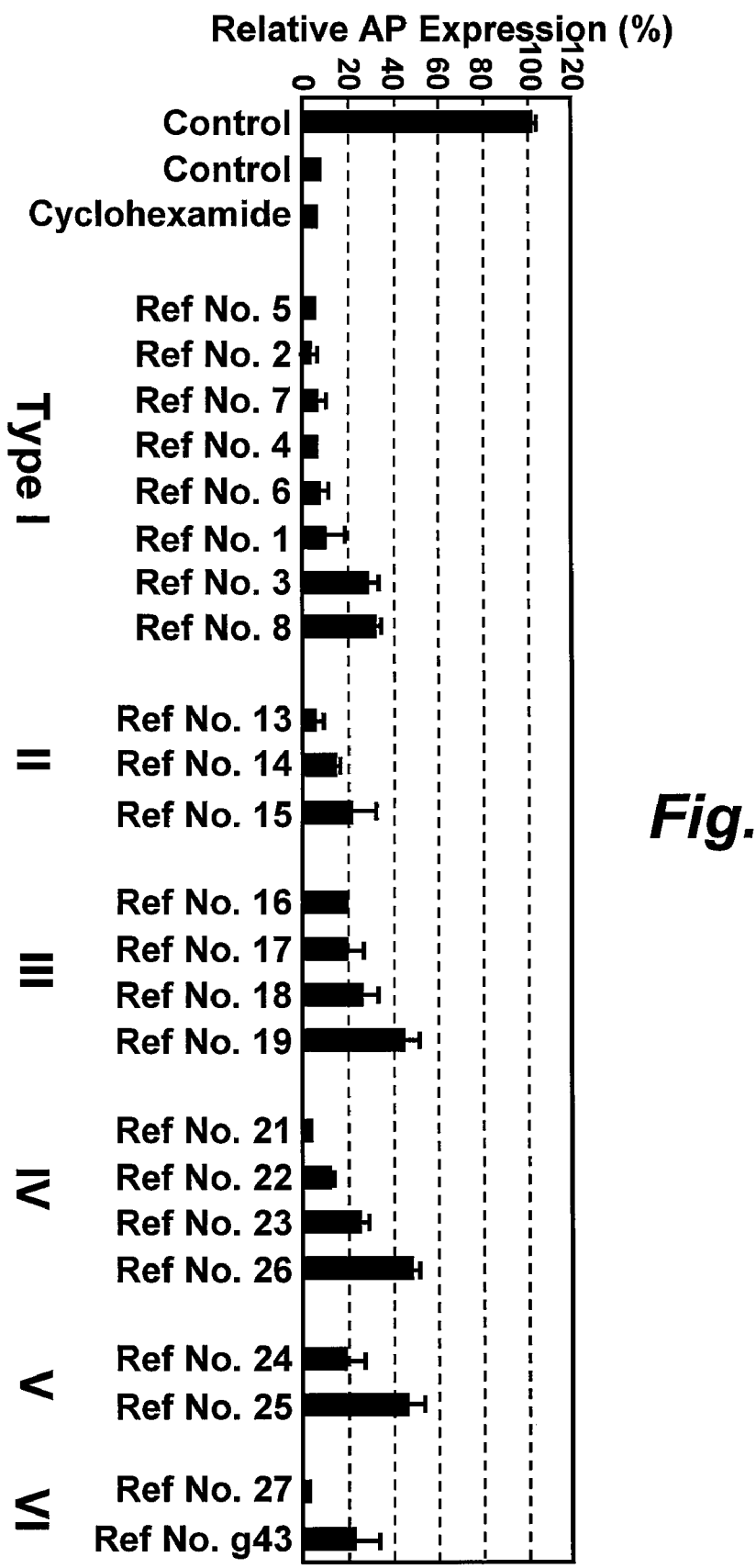
FIG. 2 is a bar chart showing inhibition of HIF-1 regulated alkaline phosphatase by the indicated compounds in genetically engineered LN229 cells.
Figure 3:
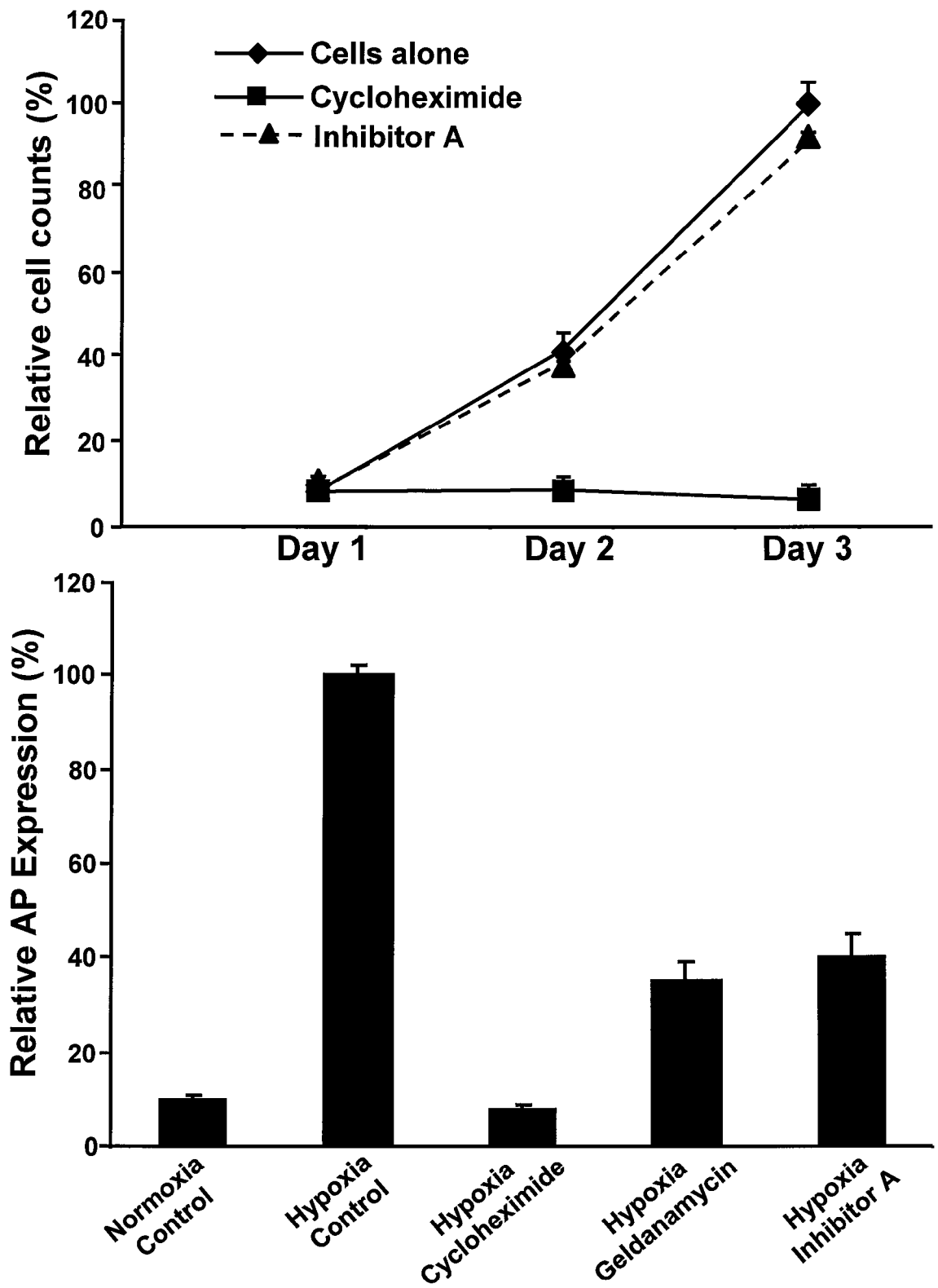
FIG. 3 is a bar graph showing the inhibition of alkaline phosphatase by an exemplary compound of the present disclosure.
Figure 4:
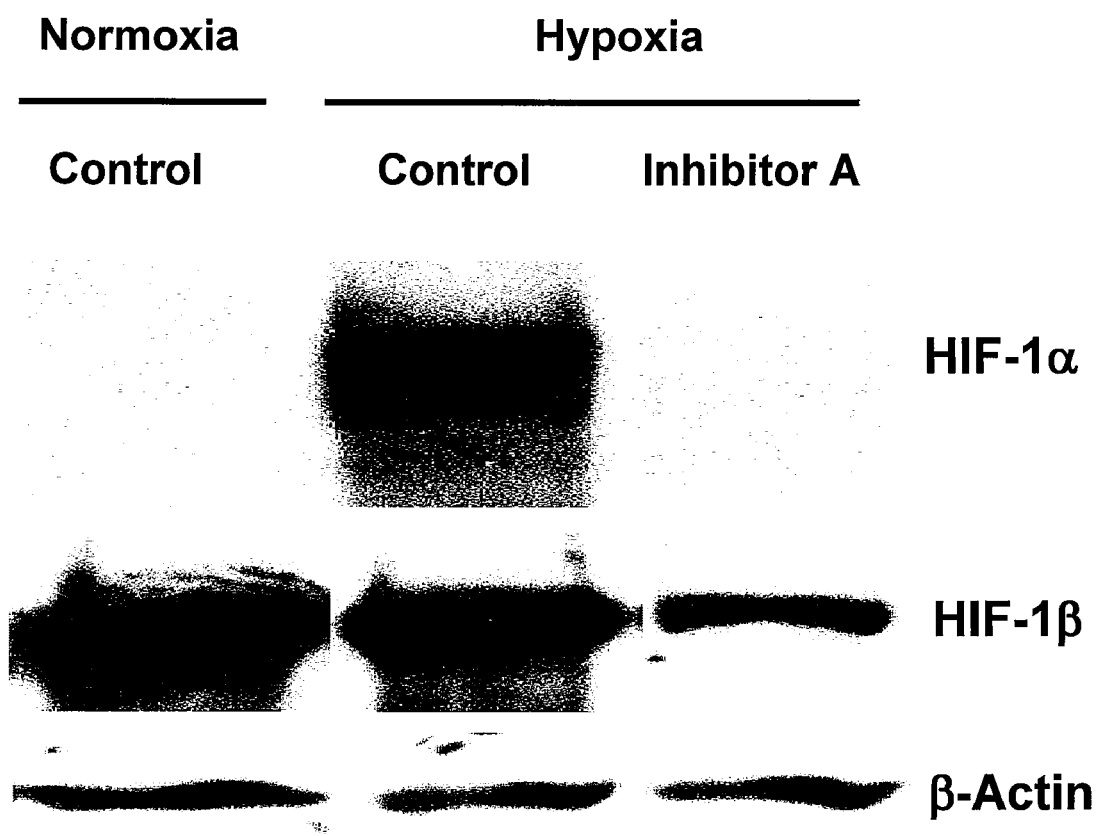
FIG. 4 is an immunoblot showing inhibition of HIF-1 protein levels by an exemplary compound of the present disclosure.

22 compounds had more than 50% inhibition on AP activity at 1 µM (FIG. 2). Compound Ref. No. 1 was further studied for its effect on HIF-1α, HIF-1β and β-actin by Western blotting (FIG. 4). LN229 cells were treated with 1 µM of compound Ref. No. 1 and incubated under hypoxia for 24 h. Compound Ref. No. 1 abrogated HIF-1α which was normally present at high levels induced by hypoxia. HIF-1β level was decreased but to a less extent, and β-actin level remained unchanged.

When the test compounds were resynthesized and re-tested for their anti-HIF-1/HRE activity, they were all less active than the original compounds. Among them, compound Ref. No. 17 was the most active with $IC_{50}$ value of 7.5 µM. At this concentration, compound Ref. No. 17 abrogated HIF-1α levels induced either by $CoCl_2$ or hypoxia. HIF-1β level was decreased but to a less extent, and β-actin level remained unchanged. Compound Ref. No. 27 has an $IC_{50}$ value of 11 µM in alkaline phosphatase reporter assay.

We claim:
1. A method of modulating HIF-1 activity in a cultured animal or human cell under hypoxic conditions comprising: contacting a cultured animal or human cell with an effective amount of a compound of the formula:

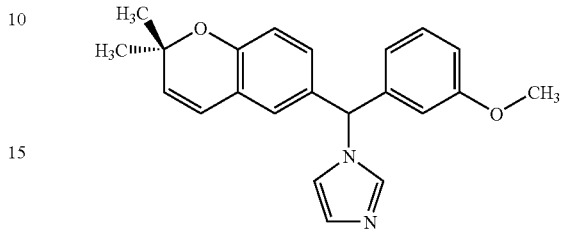

or a pharmaceutically acceptable salt, or a prodrug thereof, whereby the effective amount of the compound according to the formula:

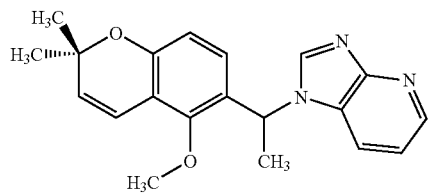

delivered reduces the amount of an HIF-1α gene-specific product expressed by the cultured animal or human cell.

2. The method according to claim 1, wherein the cultured animal or human cell receiving the compound according to formula:

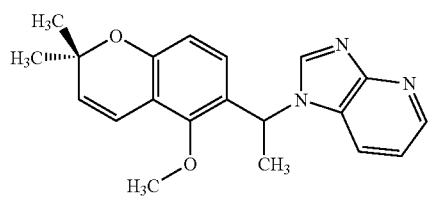

is maintained under hypoxic conditions.

* * * * *

UNITED STATES PATENT AND TRADEMARK OFFICE
CERTIFICATE OF CORRECTION

PATENT NO. : 7,652,033 B2
APPLICATION NO. : 10/550286
DATED : January 26, 2010
INVENTOR(S) : Van Meir et al.

It is certified that error appears in the above-identified patent and that said Letters Patent is hereby corrected as shown below:

On the title page item (73), should read:

Assignees: Emory University, Atlanta, GA (US)
The Scripps Research Institute, La Jolla, CA (US)

Title page, item (*) Notice: Subject to any disclaimer, the term of this patent is extended or adjusted under 35 U.S.C. 154(b) by 641 days.

Delete the phrase "by 641 days" and insert -- by 1023 days --.

Signed and Sealed this

Seventh Day of September, 2010

David J. Kappos
*Director of the United States Patent and Trademark Office*